United States Patent [19]

Hassler et al.

[11] Patent Number: 5,058,569
[45] Date of Patent: Oct. 22, 1991

[54] APPARATUS FOR GENERATING FOCUSED SHOCKWAVES HAVING A CYLINDRICAL COIL AND A PARABOLOID OF REVOLUTION REFLECTOR

[75] Inventors: Dietrich Hassler, Uttenreuth; Helmut Reichenberger, Eckental; Hubert Schwark, Buckenhof; Erhard Schmidt, Erlangen, all of Fed. Rep. of Germany

[73] Assignee: Siemens Aktiengesellschaft, Munich, Fed. Rep. of Germany

[21] Appl. No.: 558,095

[22] Filed: Jul. 26, 1990

[30] Foreign Application Priority Data

Aug. 11, 1989 [EP] European Pat. Off. ......... 89114925.4

[51] Int. Cl.⁵ .............................................. A61B 17/22
[52] U.S. Cl. ......................... 128/24 OEL; 128/660.03
[58] Field of Search ......... 128/24 EL, 660.03, 24 AA

[56] References Cited

U.S. PATENT DOCUMENTS

| 4,669,472 | 6/1987 | Eisenmenger . | |
| 4,674,505 | 6/1987 | Pauli et al. | 128/24 EL |
| 4,697,588 | 10/1987 | Reichenberger | 128/24 EL |
| 4,901,709 | 2/1990 | Rattner | 128/24 EL |
| 4,915,114 | 4/1990 | Hassler | 128/24 EL |

FOREIGN PATENT DOCUMENTS

| 3443295 | 6/1986 | Fed. Rep. of Germany . | |
| 3727692 | 3/1989 | Fed. Rep. of Germany | 128/24 EL |
| 2440227 | 5/1980 | France . | |
| 1393489 | 5/1988 | U.S.S.R. | 128/24 EL |
| 1405885 | 6/1988 | U.S.S.R. | 128/24 EL |

Primary Examiner—Lee S. Cohen
Assistant Examiner—Krista M. Pfaffle
Attorney, Agent, or Firm—Hill, Van Santen, Steadman & Simpson

[57] ABSTRACT

An apparatus for generating focused shockwaves, suitable for extracorporeal lithotripsy, has a substantially hollow-cylindrical membrane consisting of electrically conductive material and an electrical coil arrangement disposed inside the membrane which can be supplied with a high voltage pulse to rapidly repel the membrane and thereby generate a shockwave. The apparatus includes a concave reflector in the form of a paraboloid of revolution, which surrounds the membrane and coil, and which has a center axis substantially coincident with the center axis of the membrane. An acoustic propagation medium fills at least the volume between the membrane and the reflector. The shockwave generated by the cylindrical coil and membrane arrangement is reflected and focused by the paraboloid of revolution so that the shockwaves converge at a focus. The apparatus is arranged so that the focus conicides with a region of a patient to be treated with shockwave therapy, such as a calculus. The coil is wound in the shape of a cylindrical helix, and the membrane is in the form of a thin-walled, smooth tube.

14 Claims, 2 Drawing Sheets

APPARATUS FOR GENERATING FOCUSED SHOCKWAVES HAVING A CYLINDRICAL COIL AND A PARABOLOID OF REVOLUTION REFLECTOR

BACKGROUND OF THE INVENTION

1. Field of the Invention

The present invention is directed to an apparatus for generating focused shockwaves of the type suitable for use in extracorporeal lithotripsy, and in particular to such an apparatus wherein the shockwaves are electromagnetically generated.

2. Description of the Prior Art

Electromagnetic shockwave sources are known for use for a number of purposes, for example, for non-invasively disintegrating calculi situated in the body of a patient, a therapy known as extracorporeal lithotripsy, or to otherwise non-invasively treat pathological tissue with shockwaves. Such shockwave sources can also be utilized in materials testing, to charge specimens under examination with focused shockwaves. For these purposes, the shockwave source is acoustically coupled to the object which is to be irradiated with shockwaves, so that the generated shockwaves can be conducted into the object. Such electromagnetic shockwave sources generally function by supplying a coil arrangement with a high voltage pulse, as a consequence of which an electrically conductive membrane, disposed close to the coil, is rapidly radially expelled away from the coil, thereby generating a pressure pulse in the form of a cylindrical wave moving away from the membrane in a propagation medium surrounding the membrane. This pressure pulse gradually steepens to form a shockwave. The pressure pulse or shockwave is reflected by a reflecting surface so that the acoustic energy is concentrated at the focus of the reflector, such as at the focus of a paraboloid of revolution. The shockwave source and the object to be treated must be disposed relative to each other so that the region to be irradiated with shockwaves in the object coincides with the focus of the reflector. This constitutes the focal region of the shockwaves.

A shockwave source of the type described above is known as a "large aperture ring-shaped sound source" (LARS). Other types of electromagnetic shockwave sources are known wherein planar shockwaves are initially generated, which are focused with suitable acoustic lenses as described in German 33 28 039, corresponding to U.S. Pat. No. 4,674,505, or wherein a membrane shaped in the form of a portion of a spherical surface is provided, in which case further focusing is not necessary. A device of this latter type is described in German OS34 43295.

In a LARS, by contrast, cylindrical waves are generated, which are then concentrated at a focus by reflection at a reflector having the shape of a paraboloid of revolution. In a known shockwave source of this type, the coil arrangement consists of a plurality of flat coils which are arranged side-by-side in a cylindrically curved surface inside a hollow-cylindrical membrane. The manufacture of this coil arrangement involves rather considerable outlay, and thus results in an expensive device. Moreover, the space available for the coil arrangement is not completely exploited, and thus the efficiency of this known shockwave source is substantially below the theoretically possible efficiency. Additionally, it is not possible to uniformly drive the membrane along its circumference, as a consequence of the fashioning of the coil arrangement. This means that the membrane is subjected to locally differing deformations along its circumference, and is therefor exposed to unfavorable mechanical stresses which can result in a premature failure of the membrane. It has been proposed to provide the membrane with beads at those regions of the membrane coinciding with the regions at which neighboring coils of the coil arrangement adjoin, so that the membrane can be deformed more easily under the action of the driving forces. This measure, however, makes manufacture of the membrane considerably more expensive, and also deteriorates the focusing effect, because an ideal cylindrical wave cannot proceed from a membrane provided with such beads.

SUMMARY OF THE INVENTION

It is an object of the present invention to provide a shockwave source having a cylindrical coil and a paraboloid of revolution reflector which can be manufactured with low manufacturing outlay and cost, and wherein a uniform drive of the membrane is insured so that a high efficiency is achieved.

The above objects are achieved in an apparatus constructed in accordance with the principles of the present invention wherein the coil arrangement consists of at least one coil wound in the shape of a cylindrical helix, and wherein the membrane is fashioned as a thin-walled, smooth tube. Due to the fact that the coil is wound in the shape of a cylindrical helix, manufacturing outlay for the coil arrangement is as low as possible. Simultaneously, this coil structure enables an optimum exploitation of the space available for the coil arrangement, so that a high efficiency is achieved. Moreover, this coil structure assures a uniform drive of the membrane, so that the membrane is subjected to a uniform mechanical stressing by the driving forces. As a consequence, and because the membrane is a thin-walled smooth tube, it is insured that substantially ideal cylindrical waves emanate from the membrane, which are necessary for good focusing. Moreover, fashioning of the membrane as a thin-walled, smooth tube also permits the membrane to be manufactured with minimum outlay.

In a preferred embodiment, the coil is concentrically disposed relative to the membrane, which results in particularly uniform driving and stressing conditions for the membrane.

In a further embodiment of the invention, the membrane is a seamless tube. A long life of the membrane is obtained with such a structure, because a seam necessarily represents a mechanically weak location, and is thereby avoided. To further promote the emission of ideal cylindrical waves from the membrane, the membrane preferably has a constant thickness. The membrane preferably contains at least one material selected from the group consisting of aluminum, copper, silver and highly conductive alloys thereof such as, for example, bronzes. Aluminum is preferred as the material for the membrane because this material has the advantage of high electrical conductivity with good mechanical strength and processing characteristics.

The turns of the coil must have a suitable insulation to insure an adequate dielectric strength of the coil. Also, for providing sufficient dielectric strength, insulating means are disposed between the coil and the inside wall of the membrane. This can be an insulation which surrounds the wire of the coil, if this insulation has a sufficient insulating capability. Preferably, however, the insulating means are formed by an insulating foil arranged between the inside wall of the membrane and the coil.

In a preferred embodiment, the space between the inside wall of the membrane and the coil, or between the membrane and the insulating means, can be charged with a vacuum. This insures that the membrane will be disposed close to the coil before the generation of shockwave, which has a positive influence on the efficiency of the shockwave source. Use of a vacuum also insures that the membrane will be returned to a defined initial position after a shockwave has been generated, so that successively generated shockwaves have identical characteristics.

In a further embodiment, an ultrasound locating system can be provided, with which the focal region of the shockwave can be scanned. The ultrasound locating system includes an ultrasound applicator, which can be disposed inside of the cylindrical coil. This embodiment is of significance particularly if the shockwave source is to be utilized for medical purposes, for example for disintegrating calculi in the body of a patient, in which case the shockwave source will be disposed relative to the body of the patient with the assistance of the ultrasound locating system so that the target region (i.e., the calculus) is situated in the focal region of the shockwaves. A further advantage of this embodiment is that the space which is present anyway in the inside of the coil is used to accept the ultrasound applicator. No special structural measures are therefore required in order to integrate the ultrasound applicator into the shockwave source. In a further modification of the invention, the coil is wound on a coil carrier consisting of electrically insulating material which is shaped as a cylinder, at least in the region of the coil. A mechanically stable mounting of the coil is achieved by this structure in a simple way. The coil carrier may have a central bore, in which the ultrasound applicator can be disposed, if used. If the reflector (or at least the reflecting surface thereof) consists of a material, for example brass, which is acoustically harder than the propagation medium, for example water, the shockwaves emitted by the apparatus are best suited for treating a patient having calculi, bone disease, or certain types of pathological tissue. In a further modification of the invention, the reflector (or at least the reflecting surface thereof) consists of foamlike expanded cellular material having closed pores, which is acoustically softer than the propagation medium. Shockwaves generated in this embodiment have a pressure below atmospheric pressure, and are particularly suited for treating other types of pathological tissue, for example tumors, because such below-atmospheric pressure promotes the formation of cavitation which has been shown to damage cells and tissue of this type in animal experiments.

DESCRIPTION OF THE PREFERRED EMBODIMENT

Figure 1:
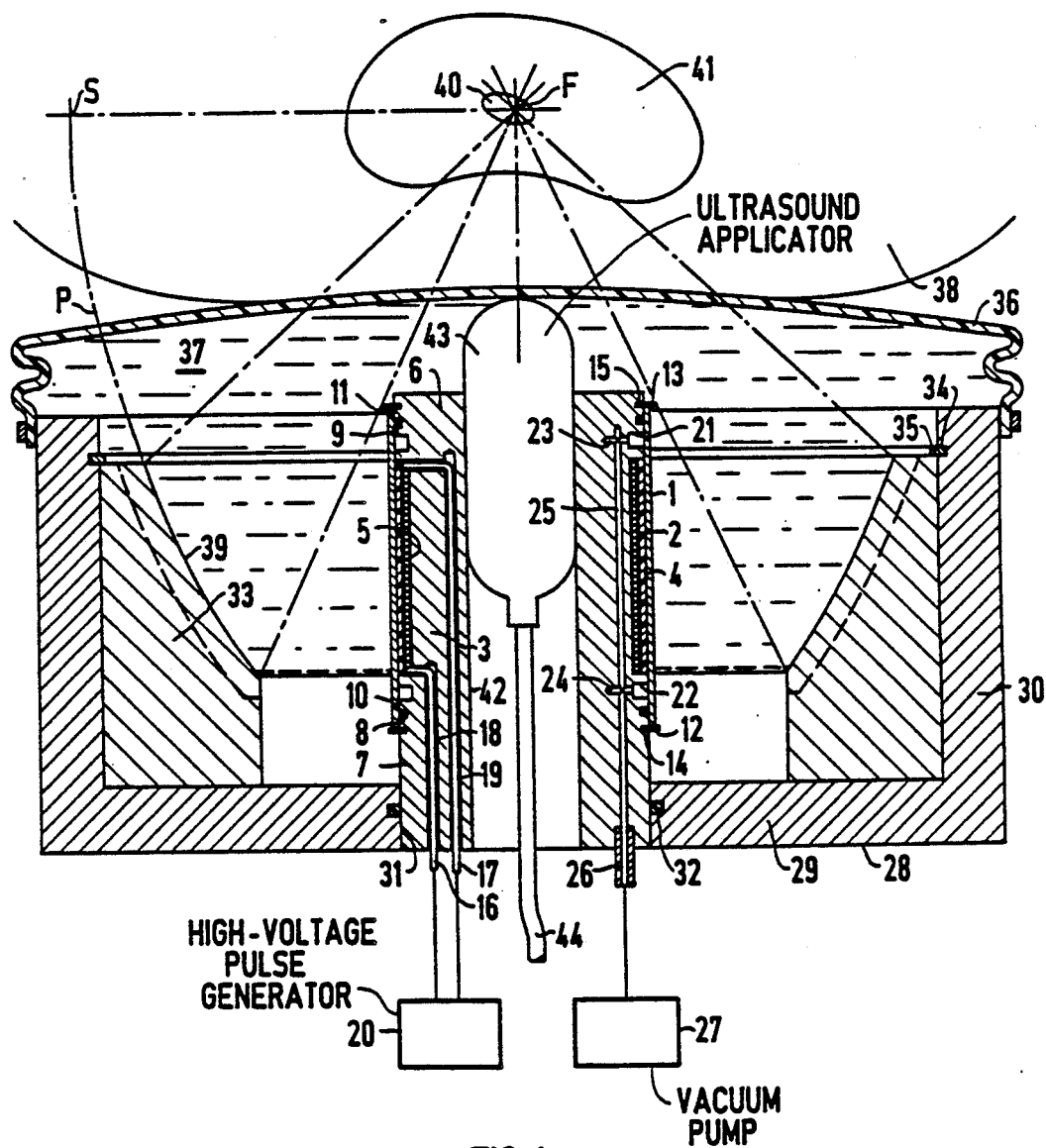
FIG. 1 is a longitudinal sectional view of an apparatus for generating focused shockwaves constructed in accordance with the principles of the present invention, in a first embodiment.

The apparatus for generating shockwaves shown in FIG. 1 has a substantially hollow-cylindrical membrane 1 consisting of electrically conductive material in the form of a thin-walled, smooth seamless tube of constant thickness. The membrane 1 contains at least one material from the group of copper, silver, and alloys thereof.

A coil 2 is disposed inside the membrane 1, the coil tube being wound in the form of a cylindrical helix on a cylindrical coil carrier 3. To avoid electrical shorts, or voltage arcing, between the turns of the coil 2, the wire of the coil 2 is provided with a lacquer insulation, with the coil 2 being preferably a lacquered copper wire. The turns of the coil are fixed on the coil carrier 3 by immersion in a suitable fixing agent or casting resin (not shown).

To avoid voltage arcing between the coil 2 and the membrane 1, when the coil 2 is charged with high voltage pulses with high amperage for generating shockwaves, the coil 2 has an outer-surface which is completely surrounded by an insulating foil 4, whose thickness is shown exaggerated in FIG. 1, as are the thickness of the membrane 1 and of the coil 2.

At its outer surface, the coil carrier 3 has an annular recess 5, in which the coil 2 and the insulating foil 4 are received. The length of the annular recess 5 is equal to the length of the coil 2. The depth of the annular recess 5 is equal to the sum of the thickness of the coil 2 and of the insulating foil 4, or may be slightly larger than this sum. At both sides of the coil 2, therefore, the coil carrier 3 has respective cylindrical shoulders 6 and 7, the diameter of the shoulders 6 and 7 being substantially the same as the inside diameter of the membrane 1. By appropriate sealing rings 10 and 11, received in respective channels 8 and 9 in the shoulders 6 and 7, the membrane 1 is placed on the coil carrier 3. The membrane 1 is axially fixed so as to be non-displaceable along the coil carrier 3 by snap rings 12 and 13, which press against the ends of the membrane 1 and which are received in corresponding channels 14 and 15 in the respective shoulders 6 and 7 of the coil carrier 3.

The terminals 16 and 17 of the coil are conducted through angled bores 18 and 19 provided in the coil carrier 3 to the end face of the shoulder 7. The terminals are then connected, as schematically indicated, to a high voltage pulse generator 20. The coil carrier 3 also has an annular channel 21 disposed between the recess 5 and the channel 9, and a channel 22 disposed between the recess 5 and the channel 8. The channels 21 and 22 communicate with bores 23 and 24, which proceed approximately radially in the coil member 3. The bores 23 and 24 are, in turn, in communication with a bore 25 which proceeds approximately axially in the core carrier 3. The bore 25 exits the carrier 3 in the region of the end face of the shoulder 7, and is connected via a line 26 to a vacuum pump, schematically indicated in FIG. 1. It is thus possible to charge the volume between the inside wall of the membrane 1 and the insulating foil 4 with vacuum.

The apparatus shown in FIG. 1 also has a housing 28, with a base 29 and a cylindrically tube-shaped wall 30. The shoulder 7 of the coil carrier 3 is fixed in a bore 31 in the base 29 of the housing 28 by a sealing ring 32, so that a center axis of the membrane 1, a center axis of the coil 2, and a center axis of the housing 28 coincide.

An annular reflector 33 is received in the housing 28, having an outer surface which presses against the inside of the wall 30. The reflector 33 has one end faced disposed against the base 29 of the housing 28, and is fixed so as to be axially non-displaceable in the housing 28 with a snap ring 35, which is accepted in a corresponding channel 34 provided in the wall of the housing 28.

The end of the housing 28 opposite of the base 29 is closed with a flexible bellows 36. The volume surrounded by the bellows 36, the housing 28, the reflector 33, the coil carrier 3 and the membrane 1 is filled with an acoustic propagation medium 37, for example water. The bellows 36 permits acoustic coupling of the shockwave source with the body 38 of a patient (or any other object to be irradiated with shockwaves). The body 38 of a patient is schematically indicated in FIG. 1 with the bellows 36 of the shockwave source shown pressed against the body.

The annular reflector 33 surrounding the membrane 1 has the shape of a paraboloid of revolution, and has a center axis coinciding with the center axis of the membrane 1 and the center axis of the coil 2. In other words, the reflector 33 has a concave reflector surface 39 obtained by a rotation of a section of a paraboloid P, indicated with dashed lines in FIG. 1, around the center axis of the membrane 1. The focus F of the paraboloid P lies on the center axis of the membrane 1, and the vertex S of the paraboloid P lies on a straight line which intersects the center axis of the membrane 1 at a right angle. It must be taken into consideration that the focus F of the paraboloid P during operation of the shockwaves source, as described below, corresponds to the center of the focal region of the generated shockwaves. Generally, the extent of the reflector face 39 and the direction of the center axis of the membrane 1 is equal to the length of the coil 2, as shown in FIG. 1. The reflector surface 39 is arranged in the axial direction relative to the coil 2 so that the edges of the reflector surface 39 and the corresponding edges of the coil 2 are disposed radially opposite each other. It is also possible, however, for the reflector surface 39 to have an extent in the direction of the center axis of the membrane 1 which is not the same as that of the coil 2, or to arrange the reflector surface 39 axially offset relative to the coil 2.

The reflector 33 (or at least the reflector surface 39 thereof) consists of a material in the embodiment of FIG. 1 which is acoustically harder than the propagation medium 37. If the propagation medium 37 is water, a metallic material such as brass may be used as the material for the reflector 33 (or the surface 39 thereof). As shown with dashed lines, it is sufficient that the harder material be provided as a layer in the region of the surface 39 of the reflector 33. In the embodiment of FIG. 1, however, the entire reflector 33 consists of metal.

Operation of the shockwave source shown in FIG. 1 is as follows.

When the coil 2 is charged with a high voltage pulse by the high voltage generator 20, the coil 2 quickly generates a magnetic field. As a result, a current is simultaneously induced in the membrane 1, in a direction opposite to the direction of the current flowing in the coil 2. The membrane consequently generates an opposing magnetic field, which causes the membrane 1 to rapidly radially expand, being repelled from the coil 2. The membrane 1 thereby generates a radially outwardly propagating pressure pulse in the shape of a cylindrical wave in the propagation medium 37. This pressure pulse, as is shown by dashed lines for the "edge rays" of the cylindrical wave in FIG. 1, is reflected at the surface of the reflector 33 so that it converges at the focus F of the paraboloid P. Along its propagation path, the pressure pulse gradually steepens, as a consequence of the non-linear compression properties of the propagation medium 37, and is converted into a shockwave. The apparatus of FIG. 1 thus generates shockwaves which converge in a focal region having a center corresponding to the focus F of the paraboloid P. Because the reflector 33 consists of a material which is acoustically harder than the propagation medium 37, the shockwaves generated in this manner will be in the form of positive pressure pulses. (As used herein, a material having a larger acoustic hardness than another material is understood as meaning that the characteristic acoustic wave impedance of the material is higher than that of the other material, such as that of the propagation medium.)

While the shockwaves are being generated, the volume between the membrane 1 and the insulating foil is charged with a vacuum by the vacuum pump 27 via the line 26 and via the bores 23, 24 and 25. This assures that the membrane 1 will be situated as close as possible to the coil 2 before the coil 2 is charged with a high voltage pulses, thereby making the shockwave source operate at high efficiency. Additionally, this insures that the membrane 1 will return to a defined initialed position after a pressure pulse has been generated.

To disintegrate a calculus situated in the body 38 of a patient, which is schematically indicated in FIG. 1 as a stone 40 of a kidney 41, the shockwave source is pressed against the body surface of the patient by the bellows 36 for acoustic coupling and is aligned so that the calculus 40 is situated in the focus F of the paraboloid P, and thus is in the focal region of the shockwaves. By the action of a plurality of successively generated shockwaves, the calculus 40 disintegrates into fragments which can be eliminated in a natural manner.

To align the shockwave source relative to the body 38 of the patient in the described way, and ultrasound locating system is provided, which includes an ultrasound applicator 43, schematically indicated in FIG. 1, disposed in a central bore 42 of the coil carrier 3. The ultrasound applicator 43 is in electrical communication with conventional ultrasound control and image-generating electronics (not shown) via a cable 44. This permits an ultrasound image of the focal region to be visually displayed. The ultrasound locating system is preferable a conventional ultrasound sector scanner, and is disposed so that a circular sector-shaped slice of the body 38 of the patient which contains the center axis of the membrane 1, and thus the focal region of the shockwaves, can be scanned.

A prototype of an apparatus constructed in conformity with FIG. 1 has an aluminum membrane with an outside diameter of 56 mm, a thickness of 0.3 mm and length of 60 mm. In the prototype, the coil 2 is wound on a coil carrier 3 consisting of resin-bonded fabric, the coil 2 consisting of wire having a circular cross-section and a diameter of 0.5 mm and consisting of three windings connected in parallel, each winding having 29 turns. The reflector is fashioned on the basis of a parabola of the second order, having a perimeter of 200 mm and an inside diameter of 168 mm at the end which faces toward the focus, and has an inside diameter of 118 mm at its other end. The distance of the focus F from the front edge of the reflector is 80 mm. The reflector 33 of the prototype consists of brass. The propagation medium 37 is water.

Figure 2:
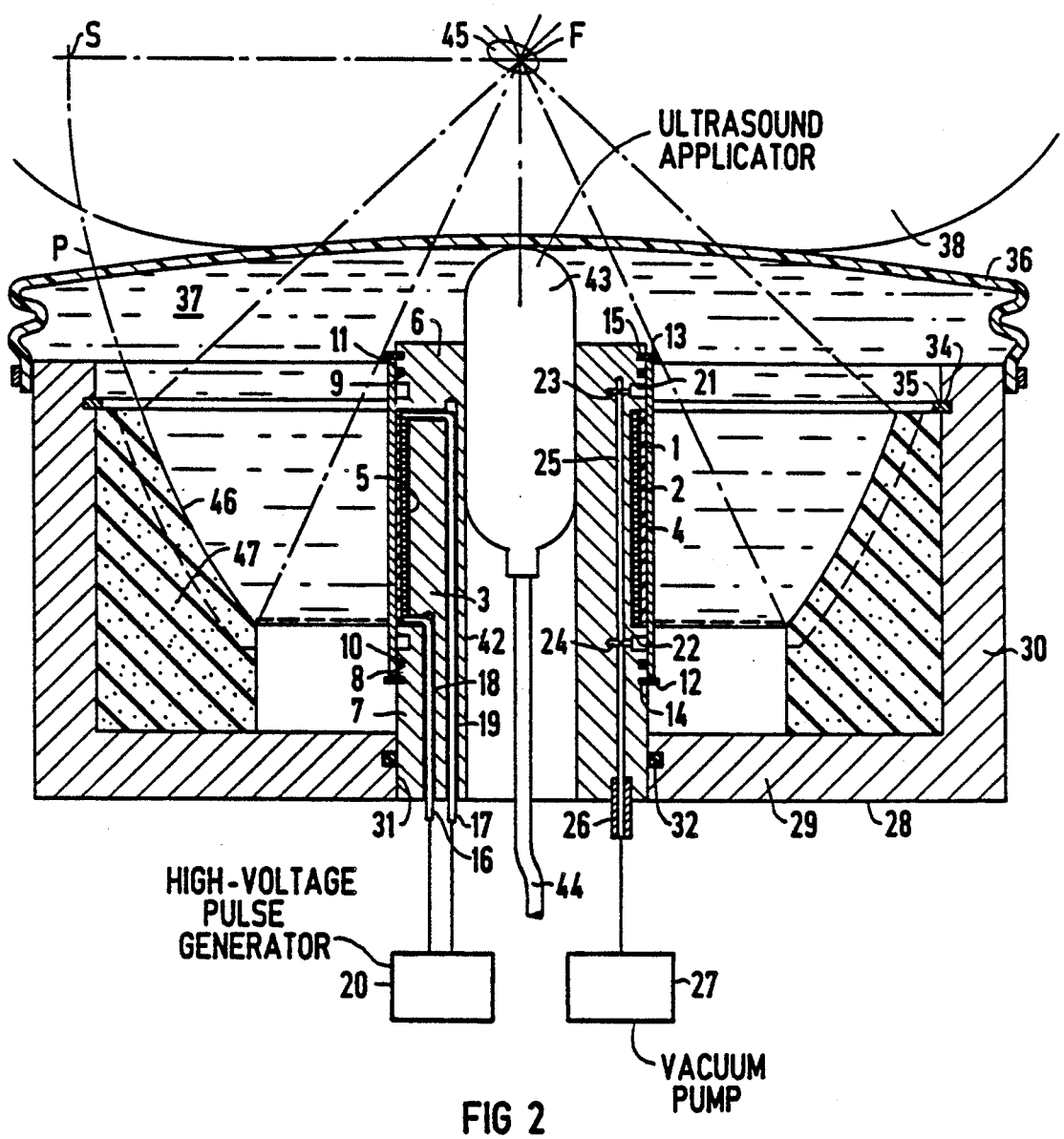
FIG. 2 is a longitudinal sectional view of an apparatus for generating focused shockwaves constructed in accordance with the principles of the present invention, in a second embodiment.

A further embodiment of an apparatus for generating shockwaves constructed in accordance with the principles of the present invention is shown in FIG. 2, which is particularly suited for irradiating pathological tissue, for example a tumor 45 situated in the body 38 of a patient. The apparatus of FIG. 2 differs from the exemplary embodiment of FIG. 1 only on the basis of the use of a different material for the reflector 47 (or at least the reflector surface 46 thereof). All remaining elements of the shockwave source of FIG. 2 have the same reference characters as in FIG. 1.

The reflector 47 in the embodiment of FIG. 2 consists of a material which is acoustically softer than the propagation medium 37. If water is used as the propagation medium 37, the material for the reflector 47 may be an expanded cellular material having closed pores such as, for example polyurethane foam. It is sufficient that the softer material be provided as a sufficiently thick layer in the region of the surface 46 of the reflector 47, as indicated by dashed lines. In the exemplary embodiment of FIG. 2, however, the entirety of the reflector 47 is shown as consisting of the softer material.

The apparatus of FIG. 2 differs in functioning from the apparatus of FIG. 1 only in that the shockwaves generated by the apparatus of FIG. 2 are below atmospheric pressure (under-pressure pulses), as a consequence of the reflector 47 consisting of material which is acoustically softer than the propagation medium 37. (as used herein, an acoustically softer material means a material having a characteristic acoustic wave impedance which is lower than that of the propagation medium.) The reason for this different type of shockwaves is that a phase reversal occurs given reflections at an acoustically soft boundary layer because the reflection factor is negative. For the reasons described above, irradiation of tumors with shockwaves in the form of below-atmospheric pressure pulses is preferred to irradiation with shockwaves having positive pressure pulses.

In the exemplary embodiments, only a single coil 2 wound in the shape of a cylindrical helix is present. It is possible, however, to provide a plurality of such coils, wound in axial succession on the coil carrier 3. Dependent on the number of coils which are supplied with high voltage pulses for the purpose of generating a shockwave, shockwaves differing in intensity can then be generated.

The reflector surface 39 (or 46) need not be exactly in the shape of a paraboloid of revolution. Alternatively, the surfaces 39 or 46 may be obtained by rotation of a section of a circle, and ellipse, or the like. The only criterion is that the reflective effect of the surface does not significantly deviate from that of a paraboloid of revolution.

Although other modifications and changes may be suggested by those skilled in the art, it is the intention of the inventors to embody within the patent warranted hereon all changes and modifications as reasonably and properly come within the scope of their contribution to the art.

We claim as our invention:

1. An apparatus for generating focused shockwaves comprising:
    a hollow-cylindrical, thin-walled smooth tubular membrane consisting of electrically conductive material, said membrane having a longitudinal center axis;
    an electrically conductive coil arrangement including at least one coil wound in the shape of a cylindrical helix inside said membrane;
    a concave reflector surrounding said membrane and having a reflecting surface facing said membrane substantially in the shape of a paraboloid of revolution and having a center axis substantially coincident with said longitudinal center axis of said membrane;
    an acoustic propagation medium filling at least the space between said membrane and said reflecting surface; and
    means for supplying said coil arrangement with high voltage pulses to rapidly repel said membrane from said coil to generate shockwaves which are focused by said reflecting surface.

2. An apparatus as claimed in claim 1 wherein said coil is disposed concentrically relative to said membrane.

3. An apparatus as claimed in claim 1 wherein said membrane is a seamless tube.

4. An apparatus as claimed in claim 1 wherein said membrane has a constant thickness.

5. An apparatus as claimed in claim 1 wherein said membrane contains at least one material selected from the group consisting of aluminum, copper, silver and bronze.

6. An apparatus as claimed in claim 1 further comprising:
    insulating means disposed between said coil and an inside wall of said membrane for electrically insulating said coil and said inside wall.

7. An apparatus as claimed in claim 6 further comprising:
    means for charging the space between said membrane and said insulating means with a vacuum.

8. An apparatus as claimed in claim 1 further comprising:
    means for charging the space between said membrane and said coil with a vacuum.

9. An apparatus as claimed in claim 1 further comprising:
    an ultrasound applicator disposed inside said coil for generating an ultrasound image containing a focus of said paraboloid of revolution.

10. An apparatus as claimed in claim 1, further comprising a coil carrier, and wherein said coil arrangement consists of electrically insulated wire wound in the shape of said cylindrical helix on said coil carrier, said coil carrier being cylindrical at least in the region of said wire.

11. An apparatus as claimed in claim 10 wherein said coil carier has a central bore, and further comprising an ultrasound applicator disposed in said central bore for generating an ultrasound image of a region containing focus of said paraboloid of revolution.

12. An apparatus as claimed in claim 1 wherein said reflecting surface consists of material which is acoustically harder than said propagation medium.

13. An apparatus as claimed in claim 1 wherein said reflecting surface consists of material which is acoustically softer than the propagation medium.

14. An apparatus as claimed in claim 13 wherein said reflecting surface consists of expanded cellular material with closed pores.

* * * * *